United States Patent [19]

Pugliese et al.

[11] Patent Number: 4,565,311

[45] Date of Patent: Jan. 21, 1986

[54] SYRINGE DISPOSAL DEVICE

[76] Inventors: Lawrence S. Pugliese, R.R. #1, Box 203B; Jerry L. Eyster, R.R. #1, both of Pittsboro, Ind. 46167

[21] Appl. No.: 588,730

[22] Filed: Mar. 12, 1984

[51] Int. Cl.⁴ .......................... B26F 3/00; B26D 9/00
[52] U.S. Cl. ........................................ 225/94; 83/167; 83/385; 83/397; 83/925 R
[58] Field of Search ................ 83/167, 382, 385–387, 83/397, 397.1, 580, 636, 925 R; 241/99; 225/94, 95, 103, 104

[56] References Cited

U.S. PATENT DOCUMENTS

| 631,832 | 8/1899 | Thackray | 83/636 |
|---|---|---|---|
| 780,097 | 1/1905 | Gernhardt | 241/99 |
| 2,776,003 | 1/1967 | Kostar | 83/54 |
| 3,404,593 | 10/1968 | Arcarese et al. | 83/167 |
| 3,469,750 | 9/1969 | Vanderbeck | 225/94 |
| 3,750,966 | 8/1973 | Anderson | 241/99 |
| 3,785,233 | 1/1974 | Robinson | 83/167 |
| 4,255,996 | 3/1981 | Choksi | 83/167 X |
| 4,275,628 | 6/1981 | Greenhouse | 83/167 |
| 4,404,881 | 9/1983 | Hanifl | 83/167 |
| 4,417,460 | 11/1983 | Moriconi | 83/167 X |

Primary Examiner—James M. Meister
Attorney, Agent, or Firm—Woodard, Weikart, Emhardt & Naughton

[57] ABSTRACT

A machine for destroying used syringes. A box includes a pair of bearing rods extending internally thereacross which slidably receive a carriage having a pair of spaced apart knives mounted thereto. A funnel mounted within the box is positioned beneath an aperture provided in the top wall of the box to receive the syringe to be destroyed. A pair of clamps mounted beneath the funnel releasably hold the syringe as the carriage moved by a linear actuator forces the knives to engage and sever in multiple locations the syringe. The clamps release the severed syringe allowing the parts to fall into a container removably positioned within the box.

12 Claims, 6 Drawing Figures

SYRINGE DISPOSAL DEVICE

BACKGROUND OF THE INVENTION

This invention is in the field of devices for cutting, smashing, or otherwise destroying syringes. Once a syringe has been used, it is desirable to destroy the syringe preventing reusage while at the same time securing the destroyed parts in such a manner to prevent contamination of a bystander or the environment. A number of United States patents disclose syringe destroyers. For example, U.S. Pat. Nos. 3,785,233, issued to Robinson; 4,275,628, issued to Greenhouse and 4,404,881, issued to Hanifl, disclose manually operated handles engaged with knives to cut a syringe thereby destroying same. U.S. Pat. No. 3,404,593, issued to Arcarese et al. discloses in addition to a manual severing device a container for catching and holding the severed parts of the syringe. U.S. Pat. No. 4,255,996, issued to Choksi et al. discloses a manually operated multiple edged knife for simultaneously severing the needle and the tubular syringe barrel which then falls into a container. A solenoid actuated syringe shearing device is disclosed in U.S. Pat. No 3,469,750, issued to Vanderbeck. Other devices have been provided to destroy syringes and are configured as a hammer mill to smash or pulverize the syringe barrel and attached needle.

A disadvantage of many of the prior syringe destroying devices is the inability to destroy different sizes of syringes with a single unit. A 60 cc syringe requires in the neighborhood of 500 pounds of force to break the needle whereas a 1 cc syringe requires only a few pounds of force. Many of the prior art syringe destroying devices are manually operated and are inadequate to provide sufficient force to destroy the larger syringes. Another disadvantage of the prior devices is the requirement for the operator to handle the syringe subsequent to the severing action. The syringe destroying device disclosed herein is electrically operated allowing for a completely hands off operation and is so constructed to exert the required force to break any size of syringe. Unlike the prior machines, the device disclosed herein encloses the syringe completely therein before, during and after the destroying or servering action. Likewise, all severed parts fall into a large container allowing for a collection of many destroyed syringes prior to removal of the container from the device. Further, due to the enclosing structure, the noise resulting from the destruction is minimized and liquids and pieces of materials are completely retained within the enclosure.

SUMMARY OF THE INVENTION

One embodiment of the present invention is a syringe destroying machine comprising an enclosure, a holder in the enclosure sized to hold a syringe including a hollow main body and attached needle and positioned to locate the syringe entirely within the enclosure, a carriage slidably mounted in the enclosure and movable to and from the holder, a knife mounted to the carriage and extending towards the holder, and electrically operated drive means connected to the carriage and operable to move the knife towards the holder to cut the syringe.

Another embodiment of the present invention is a syringe destroying machine comprising a box, a container removably positioned within the box, a bearing member mounted to the box and extending over the container, a carriage slidably mounted to the bearing member and movable at least partially across the width of the box, the box having a syringe receiving aperture through which a syringe may be inserted, electrically operated drive means mounted within the box and connected to the carriage being operable to move the carriage back and forth, closure means mounted to the box and operatively associated with the carriage to close the aperture when the carriage moves toward the syringe, and severance means mounted to the carriage and operable to sever the syringe inserted through the aperture in more than one location as the carriage moves toward the syringe.

It is an object of the present invention to provide a new and improved syringe destroying device.

A further object of the present invention is to provide an electrically operated device for destroying a variety of different sized syringes.

Yet another object of the present invention is to provide a syringe destroying device which completely encloses the syringe during the destroying step while minimizing the noise generated thereby and preventing the operator or the environment from being contaminated.

In addition, it is an object of the present invention to provide a syringe destroying device which will also retain the severed parts of a number of destroyed syringes.

Related objects and advantages of the present invention will be apparent from the following description.

DESCRIPTION OF THE PREFERRED EMBODIMENT

Figure 1:
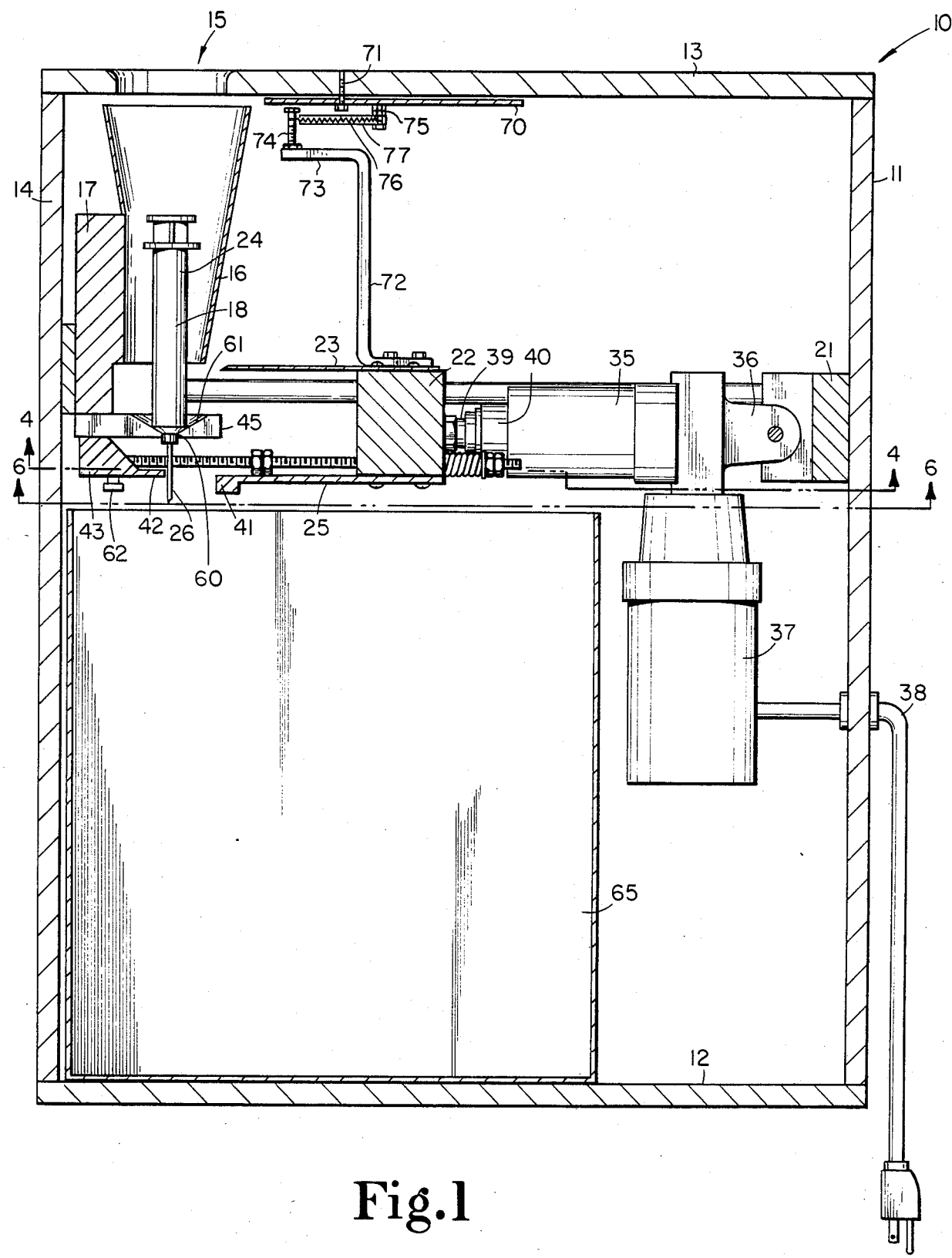
FIG. 1 is a cross-sectional view of the syringe destroying device with the syringe in place prior to destruction.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIG. 1, there is shown a syringe destroying machine 10 including a six sided enclosed box 11 having a bottom wall 12 and top wall 13 joined to four upstanding side walls 14. The top wall has an aperture 15 aligned with a funnel 16 fixedly mounted to a block 17 affixed to one of the side walls 14. Funnel 16 is sized to receive one at a time a syringe 18 which is held in position while a pair of knife edges sever the needle and main body of the syringe.

Figure 4:
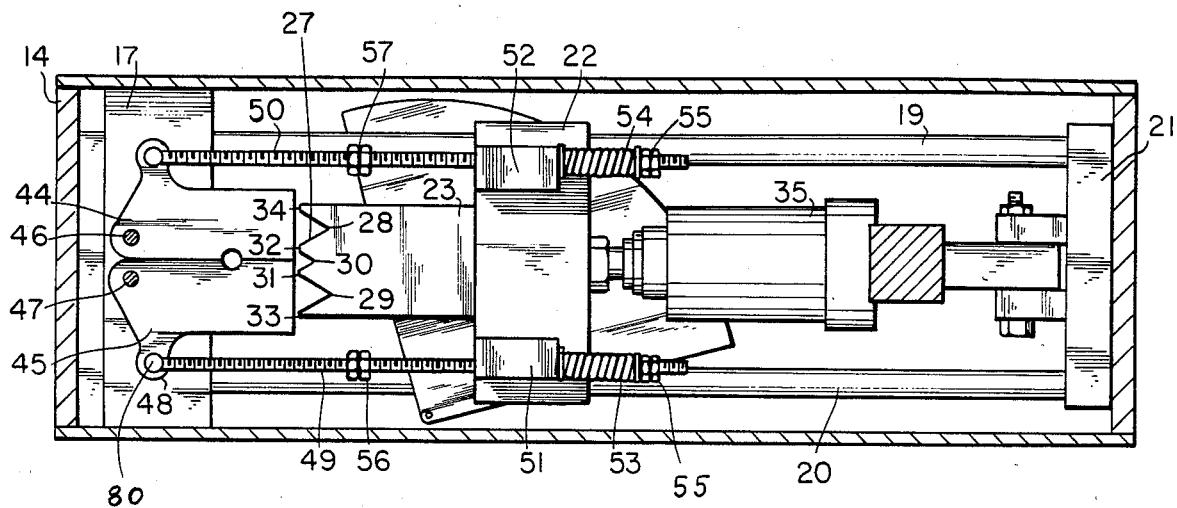
FIG. 4 is a cross-sectional view taken along the line 4—4 of FIG. 1 and viewed in the direction of the arrows.

A pair of bearing rods 19 and 20 (FIG. 4) have opposite ends fixedly secured to blocks 17 and 21 in turn secured to the end walls 14 of box 11. Rods 19 and 20 extend through carriage 22 which is slidable thereon. Carriage 22 includes bearings through which rods 19 and 20 extend to facilitate the sliding motion of the carriage relative to the bearing rods. Cantileverdy mounted to the top of carriage 22 (FIG. 1) is an upper knife 23 which is position to sever the liquid holding tubular main body 24 of syringe 18. Likewise, cantileverdly mounted to the botoom end of carriage 22 is a lower knife 25 positioned to sever the needle 26 of syringe 18. Knife 23 has a knife edge 27 (FIG. 4) with a pair of deeply extending V-shaped recesses 28 and 29 between which is located a shallow V-shaped recess 30 forming a pair of centrally located pointed edges 31 and 32 and a pair of outwardly located pointed edges 33 and 34.

Figure 5:
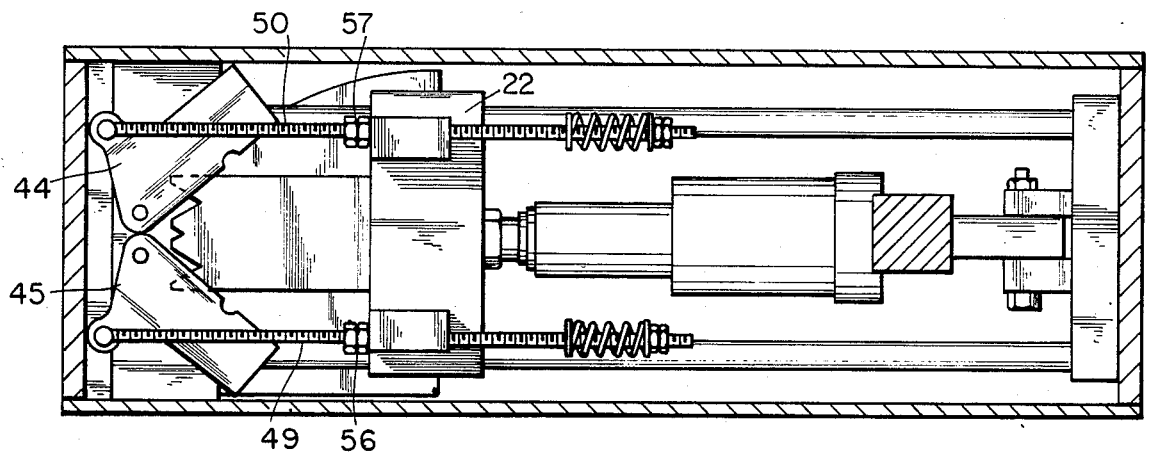
FIG. 5 is the same view as FIG. 4 only showing the knife in the inward severing position.
Figure 6:
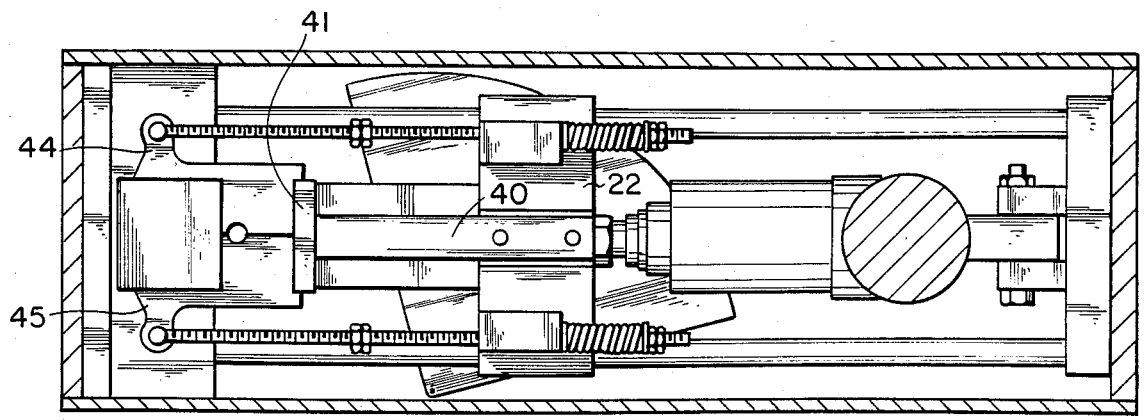
FIG. 6 is a cross-sectional view taken along the line 6—6 of FIG. 1 and viewed in the direction of the arrows.

A linear actuator 35 operated by motor 37 connected by cord 38 to a source of energy has a proximal end 36 mounted to block 21. A rod 39 extends from the distal end 40 of actuator 35 with the opposite end of rod 39 being attached to carriage 22. Thus, activation of motor 37 results in rod 39 pushing carriage 22 along with knives 23 and 25 from the retracted position of FIG. 4 toward the severing position depicted in FIG. 5 with the piston rod then being retracted to the position shown in FIG. 6 allowing the severed syringe to fall downwardly into a container 65 located beneath funnel 16. A variety of commercially available linear actuators may be utilized. In the preferred embodiment shown in the drawings, the actuator includes a worm gear structure to extend and retract rod 39.

The bottom knife 25 (FIG. 6), has T-shaped configuration including an outwardly extending plate 40 with a proximal end fixedly attached to carriage 22 and a distal end perpendicularly affixed to bar 41 positioned to slide under and against the outwardly extending and mutually facing end portion 42 (FIG. 1) of block 43 fixedly attached to and depending from block 17. Thus, as carriage 22 moves to the left as viewed in FIG. 1, the top edge of bar 41 will slide against and beneath the lower edge of end 42 of block 43 thereby breaking needle 26 into two pieces. Simultaneously, knife 23 will sever the tubular main housing 24 of th syringe into two separate pieces.

A pair of clamps 44 and 45 (FIG. 4) are pivotally connected to and beneath block 17 by pins 46 and 47. Each clamp has an outwardly extending flange pivotally receiving one end of a pair of push rods moveably by carriage 22. That is, push rods 49 and 50 have ends pivotally attached by pins 80 to ears 48 of clamps 44 and 45. Push rods 49 and 50 extend slidably freely through respectively blocks 51 and 52 mounted to and beneath carriage 22. A pair of helical springs 53 and 54 are mounted to the ends of rods 49 and 50 and are secured thereto by hexagonally shaped nuts 55. A second set of hexagonally shaped nuts 56 and 57 are mounted to rods 49 and 50 between carriage 22 and clamps 44 and 45. Since rods 49 and 50 are threaded, the hexagonally shaped nuts 55, 56 and 57 may be rotated and positioned thereon to allow adjustment of the closing and opening of clamps 44 and 45 relative to the movement of carriage 22. For example, by positioning nuts 56 and 57 closer to clamps 44 and 45, the carriage will contact nuts 56 and 57 at a location closer to the clamps thereby delaying the opening of the clamps. Likewise, by positioning nuts 55 further away from clamps 44 and 45, the carriage will contact helical springs 53 and 54 at a location farther away from the clamps thereby delaying the closing of the clamps. Thus, as the carriage moves towards the syringe from the position in FIG. 4 to the position in FIG. 5, the carriage will contact nuts 56 and 57 thereby forcing push rods 49 and 50 to the left and pivoting clamps 44 and 45 to the open position. Return of the carriage to the initial position from FIG. 5 to FIG. 6 will result in the push rods being pulled to the right thereby pivoting and closing clamps 44 and 45.

Clamps 44 and 45 have a mutually facing recess and hole extending therethrough to complementarily receive the chamfered bottom end of the tubular main body 24 of the syringe allowing the needle 26 to extend therethrough when the clamps are in the closed position. For example, clamp 45 (FIG. 1) has a hole 60 through which the needle is extendable with hole 60 being aligned with a recess formed by a diverging surface 61 to receive the beveled bottom end of syringe housing 24. Thus, when the syringe is first inserted into funnel 16, needle 26 extends through hole 60 such as shown in FIG. 1. An electrically operated needle detector 62 is mounted to the bottom end of block 43 and is operable to detect the presence of needle 26. The detector may take the form of either a microswitch or an infrared light with sensor.

Figure 2:
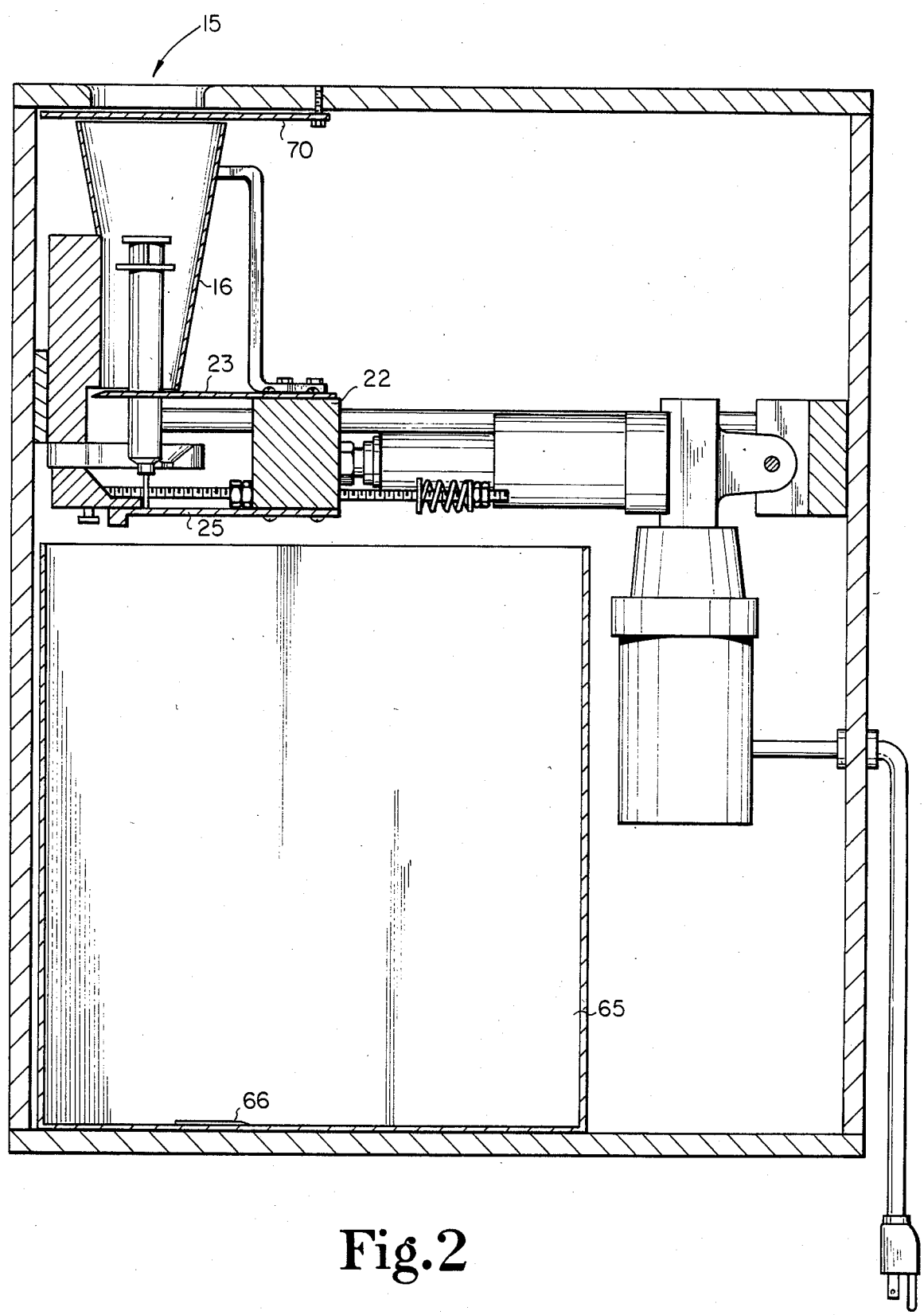
FIG. 2 is the same view as FIG. 1 only showing the needle and syringe main body being severed.
Figure 3:
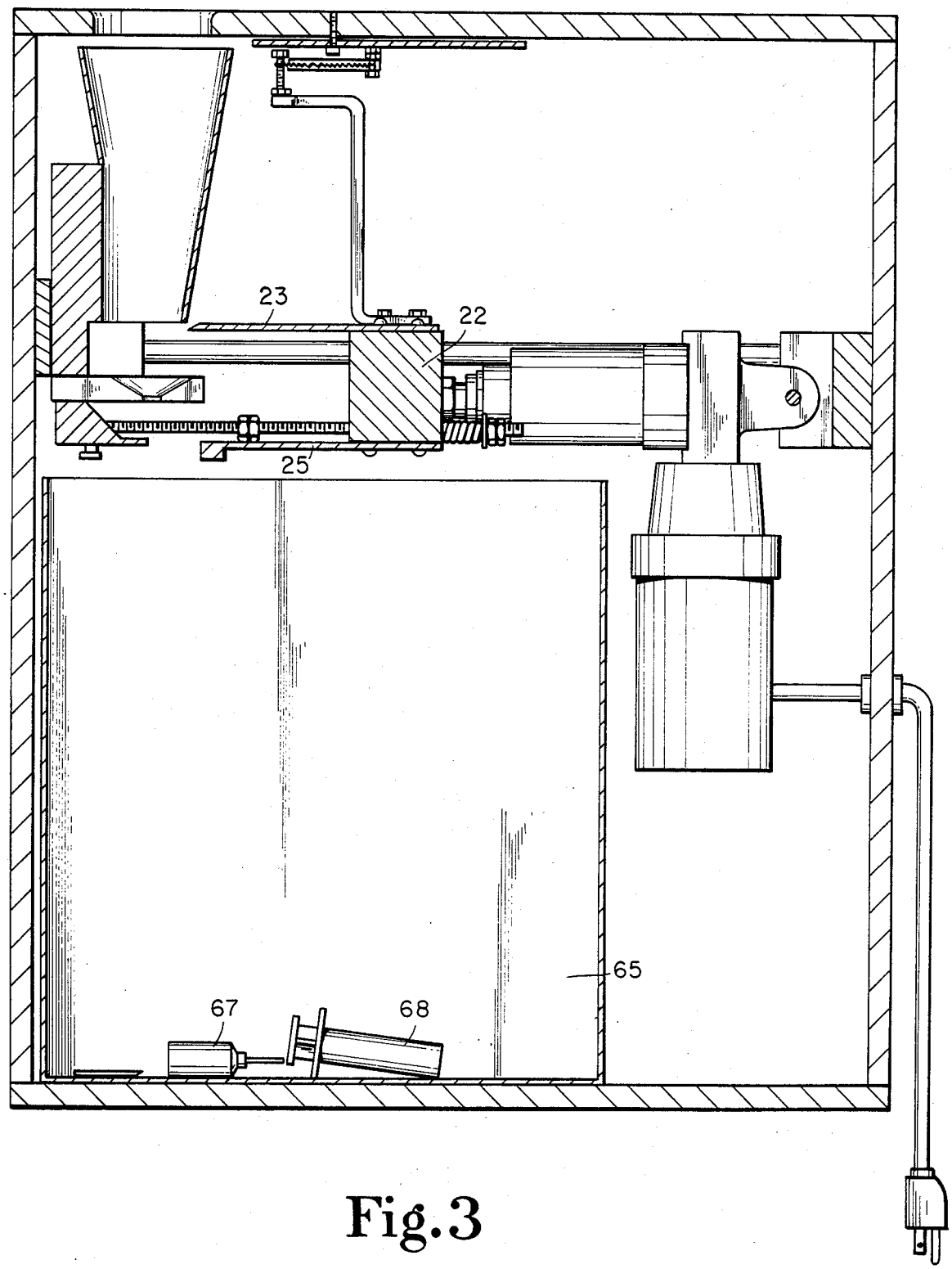
FIG. 3 is the same view as FIG. 2 only showing the knife in the retracted postion and the servered syringe retained by the storage container.

Upon detection of needle 26 by detector 62, motor 37 is activated thereby causing the linear actuator 35 to move carriage 22 to the left from FIG. 1 to FIG. 2 thereby causing the upper and lower knife to sever respectively the main housing 24 and needle 26 of the syringe. Simultaneously, clamps 44 and 45 open to the position of FIG. 5 which corresponds to the position shown in FIG. 2. Suitable limit switches are positioned to reverse the direction of travel of carriage 22 or linear actuator 35 has built within the actuator switches to reverse the direction of rod 39 once the syringe is severed. Thus, carriage 22 is caused to move to the right from the position illustrated in FIG. 2 to the position illustrated in FIGS. 3 and 6 thereby again closing the clamps. A relativly tall container 65 is removably positioned within box 11 to catch the severed portion 66 of the needle and to then catch the two severed portions 67 and 68 of the syringe (FIG. 3) once the knives have moved to the right beyond the syringe positioned in funnel 16. Nuts 55 are positioned on the push rods 49 and 50 to allow the clamps to remain open until the syringe falls therethrough into the container. Continued rightward movement of the carriage ultimately results in the carriage contacting helical springs 53 and 54 thereby causing the clamps to close. A suitable hinged door is provided on box 11 to allow removal of storage container 65 once the container is filled with destroyed syringes.

A plate shaped door 70 is pivotally mounted by fastening device 71 (FIG. 1) to and beneath the top wall 13 of the box or enclosure. An upwardly extending arm 72 having a bottom end fixedly attached to carriage 22 has a top end 73 with an upwardly extending finger 74 mounted thereon. A helical spring 76 has one end attached to finger 74 and an opposite end attached by fastening device 75 to door 70. Movement of carriage 22 and finger 74 to the left as viewed in FIG. 1 causes the helical spring to force the door to the closed position such as shown in FIG. 2. A rigid sleeve 77 encircles helical spring 76 and is operable when contacted by finger 74 to return the door from the closed position shown in FIG. 2 to the open position shown in FIG. 3.

It will be obvious from the above description that the present invention provides a new and improved syring enclosure which is designed to completely enclose the syringe prior to, during and after the destruction of the syringe. It will be further obvious from the above description that the present invention provides a syringe destroying machine which is operable to sever a syringe in multiple locations regardless of the size of the syringe. Likewise, it will be obvious from the above description that the syringe destroying machine disclosed herein allows hands off operation during and after the severance step. An alternate design of the syring destroying machine is disclosed in the Disclosure Document deposit number 121362 dated Oct. 1, 1983 and filed in the U.S. Patent and Trademark Office with said document being incorporated herein by reference.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. The syringe destroying machine comprising:
   an enclosure;
   a holder in said enclosure sized to hold a syringe including a hollow main body and attached needle and positioned to locate said syringe entirely within said enclosure;
   a carriage slidably mounted in said enclosure and moveable to and from said holder;
   a knife mounted to said carriage and extending towards said holder;
   electrically operated drive means connected to said carriage and operable to move said knife towards said holder to cut said syringe; and,
   a sliding door mounted to said enclosure and connected to said carriage being moveable over said holder to retain said syringe within said holder while being cut.

2. The syringe destroying machine comprising:
   an enclosure;
   a holder in said enclosure sized to hold a syringe including a hollow main body and attached needle and positioned to locate said syringe entirely within said enclosure;
   a carriage slidably mounted in said enclosure and moveable to and from said holder;
   a knife mounted to said carriage and extending towards said holder;
   electrically operated drive means connected to said carriage and operable to move said knife towards said holder to cut said syringe; and,
   releasing means connected to said holder and operable to release said syringe once cut by said knife allowing said syringe to fall downwardly therefrom.

3. The machine of claim 2 and further comprising:
   a removable container positioned beneath said holder to catch said syringe once cut.

4. The machine of claim 2 wherein said holder includes a pair of clamps pivotally mounted to said enclosure and connected to said carriage which open as said carriage moves towards said holder and said knife cuts said hollow main body and which close as said carriage moves away therefrom with said syringe falling downwardly therefrom.

5. A syringe destroying machine comprising:
   a box;
   a container removably associated with said box;
   a bearing member mounted to said box and extending over said container;
   a carriage slidably mounted to said bearing member and moveable at least partially across the width of said box, said box having a syringe receiving aperture through which a syringe may be inserted;
   electrically operated drive means mounted to said box and connected to said carriage being operable to move said carriage back and forth;
   closure means mounted to said box and operatively associated with said carriage to close said aperture when said carriage moves towards said syringe; and,
   severance means mounted to said carriage and operable to sever said syringe inserted through said aperture in more than one location as said carriage moves toward said syringe.

6. The machine of claim 5 wherein said severance means includes a multi-pointed knife edge mounted to said carriage and a straight needle engaging edge mounted to said carriage and spaced apart from said multi-pointed knife edge.

7. The machine of claim 6 wherein said closure means includes a door movably mounted within said enclosure and connected to said carriage.

8. The machine of claim 7 wherein said holder includes clamping means moveably mounted within said box and connected to said carriage being operable to hold said syringe upright and perpendicular to said multi-pointed edge and said needle engaging edge until said syringe is severed thereby and then operable to open and release said syringe as said carriage moves away therefrom allowing said syringe to drop into said container.

9. The machine of claim 8 wherein said holder includes a funnel mounted in said box and aligned with said aperture but being spaced therefrom to allow said door to move therebetween.

10. The machine of claim 9 and further comprising adjustment means associated with said clamping means and said carriage to allow adjustment of the opening and closing of said clamping means relative to the movement of said carriage.

11. The machine of claim 10 wherein said clamping means includes a pair of threaded rods connected to said carriage.

12. A machine for destroying the tubular main body and needle of a syringe comprising:
   an enclosure;
   a holder in said enclosure sized to hold a syringe with a hollow main body and attached needle with said holder positioned to locate said syringe entirely within said enclosure;
   a carriage moveably mounted in said enclosure and moveable to and from said holder;
   a knife mounted to said carriage and extending toward said holder;
   electrically operated drive means connected to said carriage and operable to move said knife toward said holder to cut said syringe; and
   a moveable door mounted to said enclosure and being moveable over said holder to retain said syringe within said holder while being cut.

* * * * *